United States Patent [19]

Harandi

[11] Patent Number: 5,227,534
[45] Date of Patent: Jul. 13, 1993

[54] ETHER PRODUCTION WITH MULTI-STAGE REACTION OF OLEFINS

[75] Inventor: Mohsen N. Harandi, Longhorne, Pa.

[73] Assignee: Mobil Oil Corporation, Fairfax, Va.

[21] Appl. No.: 817,187

[22] Filed: Jan. 6, 1992

Related U.S. Application Data

[63] Continuation-in-part of Ser. No. 570,744, Aug. 22, 1990, Pat. No. 5,091,590.

[51] Int. Cl.$^5$ ............................................. C07C 41/54
[52] U.S. Cl. .................................. 568/697; 585/329; 585/331
[58] Field of Search ................ 568/697; 585/329, 331

[56] References Cited

U.S. PATENT DOCUMENTS

| | | | |
|---|---|---|---|
| 4,377,393 | 3/1983 | Schleppinghoff | 568/697 |
| 4,740,632 | 4/1988 | Anderson et al. | 568/697 |
| 4,761,504 | 8/1988 | Pujado | 568/697 |
| 4,826,507 | 5/1989 | Harandi et al. | 568/697 |
| 4,868,342 | 9/1989 | Verson | 568/697 |
| 5,015,782 | 5/1991 | Harandi et al. | 568/697 |

Primary Examiner—Marianne M. Cintins
Assistant Examiner—Kimberly J. Kestler
Attorney, Agent, or Firm—Alexander J. McKillop; Malcolm D. Keen; L. G. Wise

[57] ABSTRACT

A process for upgrading olefin feedstock containing a mixture of diene, iso-olefin and linear olefin to produce tertiary-alkyl ether and high octane gasoline components comprising iso-olefin. Product recovery is integrated between primary and secondary reaction stages.

In a preferred embodiment, a two stage etherification process employs a secondary solid acid regenerable catalyst bed to etherify and/or oligomerize unconverted diene, and optionally, iso-butene in the debutanizer overhead stream of a conventional MTBE primary reactor stage. Both stages can utilize a regenerable acid catalyst such as ZSM-5 or Zeolite Beta for etherification and to upgrade unconverted alkenes and methanol from the primary stage.

20 Claims, 2 Drawing Sheets

ETHER PRODUCTION WITH MULTI-STAGE REACTION OF OLEFINS

REFERENCE TO COPENDING APPLICATION

This application is a continuation-in-part of U.S. Pat. application Ser. No. 07/570,744 filed 22 Aug. 1990, incorporated hereby by reference, now U.S. Pat. No. 5,091,590.

FIELD OF THE INVENTION

The present invention relates to a multi-stage process for preparing tertiary alkyl ethers in high yield. In particular, it relates to catalytic conversion of a mixture of isomeric mono-alkenes and diene by reaction with alkanol under etherification conditions, followed by selective etherification and/or oligomerization and alkylation of unreacted diene and iso-alkene from the primary stage.

BACKGROUND OF THE INVENTION

Recent efforts have been made in the field of gasoline blending to increase gasoline octane performance without the addition of deleterious components such as tetraethyl lead and benzene. It has been found that lower molecular weight unsymmetrical ethers such as MTBE and TAME can be added to $C_5$-$C_{10}$ hydrocarbon-containing gasoline products in order to increase octane number. The research octane number (RON) of MTBE has been listed at 115 (Lander, E. P. et al, "National Petroleum Refiners Association Annual Meeting", San Francisco, Calif., Mar. 20-24, 1983). The blending octane number of MTBE has been calculated over various concentrations and some of the readings are: RON, 115-135; MON (motor octane number), 98-110; and (RON & MON)/2, 106-122.5 (Pecci, G. et al, *Hydrocarbon Processing*, 1977, 56, 98). Blending octane number rises when MTBE concentration is decreased and saturates concentration of the base fuel is increased.

Conventional etherification processing uses as catalyst a macroreticular cation exchange resin in the hydrogen form. An example of such a catalyst is "Amberlyst 15". A resin catalyst gives a high conversion rate but is unstable at elevated temperatures (above about 90° C.). When overheated, the resin catalyst releases sulfonic and sulfuric acids. In addition leaching of acid substances from the resin catalyst even at normal operating temperatures causes a reverse reaction—decomposition of ether products to starting materials—to occur upon distillation of ether product. Overall yield is thereby significantly decreased (see U.S. Pat. No. 4,182,913 to Takesono et al).

Etherification reactions conducted over a resin catalyst such as "Amberlyst 15" are usually conducted in the liquid phase below a temperature of about 90° C. and at a pressure of about 200 psig. Equilibrium is more favorable at lower temperatures but the reaction rate decreases significantly. Also excess methanol appears to be required to achieve acceptable selectivity over "Amberlyst 15" (see Chu et al, *Industrial Engineering and Chemical Research*, vol 26, No. 2, 1987, 365-369).

Some recent efforts in the field of etherification reactions have focused on the use of acid medium-pore zeolite catalyst for highly selective conversion of n-alkene and iso-alkene with lower aliphatic alcohol starting materials. Examples of such zeolite catalysts are ZSM-4, ZSM-5, ZSM-11, ZSM-12, ZSM-23, ZSM-35, ZSM-50, zeolite Beta and MCM-22. Due to lower acidity as compared to resin catalysts, the zeolites need to be employed at higher reaction temperature to achieve the desired conversion rates. These solid acid catalyst particles are much more thermally stable than resin catalyst, are less sensitive to methanol-to-alkene ratio, give no acid effluent, and are easily and quickly regenerated (see Chu et al, "Preparation of Methyl tert-Butyl Ether (MTBE) over Zeolite Catalysts", *Industrial Engineering and Chemical Research*, op cit.). Etherification of isoalkenes and n-alkenes with medium pore zeolites is disclosed in U.S. Pat. No. 4,605,787 (Chu and Kuehl) and U.S. Pat. No. 4,714,787 (Bell et al).

Coconversion of etherification effluent from MTBE production is described in U.S. Pat. Nos. 4,788,365; 4,826,507; and 4,854,939 (Harandi et al), wherein unreacted oxygenates and olefins are upgraded in a second zeolite catalyst stage under high temperature reaction conditions to obtain aromatics-rich $C_5+$ hydrocarbon components suitable for use in blending high octane gasoline. This technique is advantageous for eliminating costly methanol and other oxygenates recovery and converting the unconverted butene to higher molecular weight products.

It has been discovered that 2-stage ether and gasoline production can be enhanced by upgrading etherification effluent under controlled moderate severity reaction conditions to oligomerize and etherify isoalkene and diene, thereby producing a second stage effluent rich in high octane $C_5+$ branched hydrocarbons and additional t-alkyl ether products. Under selected reaction conditions, it is possible to effect the isoalkene and dienes oligomerization, etherification and alkylation of olefins with alkanol without forming a large amount of aromatic or low octane linear olefins products. One important aspect of this invention is its ability to remove iso-olefins and dienes from linear aliphatics, which typically are blended into gasoline. Iso-olefins and dienes are highly reactive gasoline components in the atmoshpere, and their removal from gasoline pool hydrocarbons is important in production of clean fuels.

SUMMARY OF THE INVENTION

A multistage process has been found for etherifying a mixed $C_4+$ or $C_5+$ olefinic hydrocarbon feedstock containing diene, isoalkene and n-alkene. In a preferred embodiment, the process includes the steps of: contacting the olefinic feedstock and aliphatic alcohol ($C_1$-$C_4$ alkanol) in a first reaction stage reaction zone under partial etherification conditions with acid etherification catalyst to convert a major amount of the isoalkene to $C_5+$ tertiary-alkyl ether; recovering a reactant effluent from the first stage containing tertiary-alkyl ether product, unreacted alcohol and unreacted olefin including n-alkene; separating an ether-rich $C_5+$ liquid product stream from the first stage effluent; reacting the first stage effluent under low severity dimerization conditions at moderate temperature in a secondary stage catalytic reaction zone containing porous solid acid oligomerization catalyst; oligomerize at least a portion of diene with concurrent reaction with alkanol to etherify and/or alkylate the olefinic components; recovering a $C_5+$ liquid hydrocarbon stream oxygenates and/or oligomers from secondary stage effluent; and recovering n-alkene substantially free of diene from secondary stage effluent.

In the preferred embodiment the alcohol consists essentially of methanol, the secondary stage catalyst comprises medium pore zeolite and the primary stage catalyst comprises polymeric sulfonic acid resin, and the mixed olefin feedstock consists predominantly of $C_4$ hydrocarbons containing butadiene, isobutene and n-butene. The butadiene content of the feed ranges from 0.1% to 50% and typically about 0.3–1%.

DRAWING

FIG. 1 is a schematic diagram of a preferred embodiment of the present process, showing major operating units and flow of reactants and chemical products; and FIG. 2 is a detailed equipment diagram for a preferred fixed bed reactor arrangement.

DETAILED DESCRIPTION OF THE INVENTION

Figure 1:
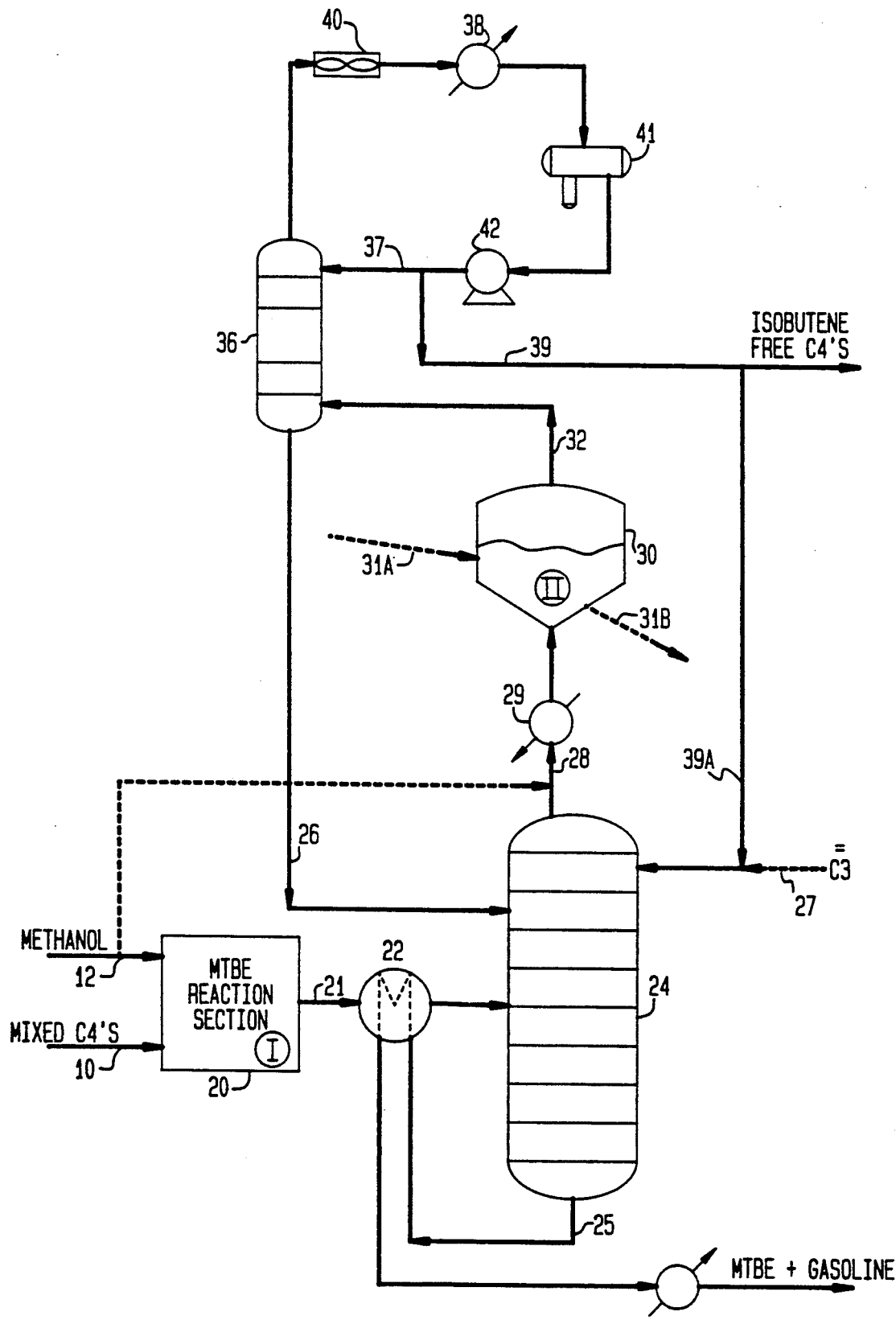

While the invention can be employed with various $C_4$–$C_7$ olefins, primary attention is directed to $C_4$ streams containing butadiene, isobutene, 1-butene and/or 2-butene. In a preferred embodiment, the present inventive process relates to the preparation of MTBE. Two reaction stages are maintained in series arrangement. The first reaction stage contains solid acid etherification catalyst particles. The second reaction zone contains medium pore zeolite solid acid catalyst, such as a fluidized bed of zeolite beta, ZSM-5 or the like. Mixed feedstock containing methanol and $C_4$ hydrocarbons, including butadiene, n-butenes and isobutene, is contacted with solid catalyst particles in the first stage reaction zone under etherification conditions to obtain an intermediate product comprising MTBE and unreacted feedstock, including about 0.2–20% butadiene, 1 to 55% of isobutene in the fresh feedstock and excess methanol. The intermediate product is then withdrawn from the first stage reaction zone, fractionated to recover MTBE, and added to the second stage catalyst zone for contact with acid catalyst under controlled severity reaction conditions. A product containing methylethers, oligomers and $C_{5+}$ alkylate is then withdrawn from the second reaction zone. The second stage product may be prefractionated to recovery unreacted butenes and other $C_4$- components.

The preferred present process further comprises replenishing or regenerating the solid catalyst particles in the second stage reaction zone. The preferred medium pore solid acid catalyst particles are aluminosilicate zeolites selected from ZSM-5, ZSM-11, ZSM-50, zeolite Beta, MCM-22 and mixtures thereof, especially the finely divided particles useful as additives in cracking heavy petroleum (FCC) materials. Therefore, the catalyst withdrawn from the second stage reactor can be used as FCC catalyst additive.

Since the mixed olefinic feedstock obtained from FCC light crackate gas contains many impurities, even after treatment in a "Merox" unit and a water wash, the solid acid zeolite catalyst from the second stage may also be employed in a guard chamber for pretreating etherification feed, whereby the zeolite becomes highly contaminated after a period of on-line contact with etherification feedstock. Some of the impurities which may be absorbed on the zeolite particles in a guard chamber include nitrogen and oxygenated compounds; metals such as Al, Fe, Na and Mg; and oligomers of olefins and diolefins, such as isoprene and cyclopentadiene. It is therefore an additional objective of the present process to remove feedstock impurities with second stage zeolite in a guard chamber contact zone concurrently with the preparation of ethers.

The first stage etherification reaction zone preferably comprises a plurality of catalytic fixed bed reactors operatively connected in series for inter-reactor cooling.

In an alternative embodiment, the second stage reaction zone comprises a moving bed, slurry, fluidized bed, or ebullated bed. The most preferred second state reactor is within the scope of the present process and apparatus to adjust the number and types of reactors which contain acid zeolite catalyst in order to optimize both product yield and overall energy consumption as would be practiced by one skilled in the art.

Optional catalyst regeneration can be achieved by contacting contaminated zeolite catalyst particles with oxygen or oxygen-containing gas in a regeneration zone under conditions of temperature and pressure sufficient to remove at least a major amount of impurities from the catalyst particles. Typical oxidative regeneration conditions are 700°–950° F. and 0–200 psig. In an alternative embodiment zeolite catalyst particles can be regenerated by stripping with a hot stream of hydrogen gas at a temperature of about 700° F. to 1000° F. Hydrogen stripping avoids the problem of inactivating the catalyst by "steaming" which can occur under oxidative regeneration conditions due to water formation. If the zeolite catalyst is not reused in the second stage conversion reactor or guard chamber contact zone, it may be passed without regeneration directly or indirectly to the associated FCC unit for cracking petroleum fractions.

The primary stage reaction zone contains an acid resin catalyst which is preferably a macroreticular polystyrene sulfonic acid resin catalyst in one or more fixed bed catalytic reactor units, most preferably only in the last stage of the etherification reactor. The primary reactor section is preferably operated at a temperature of about 40° to 90° C. Primary reactor configuration can take many forms, for example, fixed bed or stirred slurry (see U.S. Pat. No. 3,940,450 to Lee), swing or ebullated bed. It is within the scope of the present process to employ for the primary stage reaction zone any reactor configuration for sequencing acceptable to the skilled engineer.

The secondary stage feed may be vapor, liquid or mixed phased fluid. The reaction is preferably operated in a vapor phase above 110 psia for a feed containing more than 10% $C_4$- components. The reaction takes place at 70°–280° C. start of cycle temperature for a fixed bed reactor. Space velocity is 0.5–50 WHSV based on total olefins present in the feed. As catalyst is deactivated the reaction temperature can be increased. As the reaction temperature is increased ether production is reduced while alkylation and oligomerization are enhanced. Alternatively, if a fluid bed reactor is used the catalyst activity can be adjusted to maintain 70°–280° C. operating temperature.

In a preferred embodiment the olefinic feedstock comprises isobutene in an amount of at least about 10 wt. %, preferably about 25 to 40%.

Although the preferred alcohol is methanol, suitable lower aliphatic alkanols include ethanol or isopropanol (isopropyl alcohol). Of course, use of these substitutes will yield different ether products. It is within the scope of the present process to employ a mixture of lower molecular weight alcohols. Although isomeric butenes are the preferred hydrocarbon feed, other iso-olefin such as $C_5$ amylenes containing n-amylene and 3-methyl-2-butene can be etherified in the present process.

The multi-stage reactor system includes a first stage reactor containing acid etherification catalyst in a first reaction zone, including means for feeding and contacting the olefinic feedstock and aliphatic alcohol under partial etherification conditions to convert a major amount of the isoalkene to liquid tertiary-alkyl ether, and means for recovering a reaction effluent stream from the first stage containing tertiary-alkyl ether product, unreacted alcohol and unreacted olefin including n-alkene.

Referring to FIG. 1, a pre-washed $C_4$ hydrocarbon feedstock stream 10 is combined with a lower molecular weight aliphatic alcohol (methanol) feedstock 12. The combined reactants enter reaction zone 20. An acid etherification catalyst such as polysulfonic acid resin is contained in reaction section 20, which includes at least one primary etherification zone (I). The mixed alcoholic $C_4$ hydrocarbon feedstream contacts the solid catalyst within the primary reaction section 20 at predetermined reaction zone conditions of temperature and pressure to convert at least a portion of the feedstream to MTBE. Stage I effluent may be separated in a first fractionator column operatively connected to receive the reaction effluent stream from the first stage including means for recovering an ether-rich liquid product bottom fractionator stream and an overhead fractionator stream containing unreacted alcohol and feedstock olefins. An intermediate primary reaction stream 21 containing MTBE and unreacted $C_4$ hydrocarbons and alcohol is cooled in heat exchanger 22 before entering debutanizer fractionation tower 24 at a midstage thereof for recovering a product stream 25 rich in tertiary ether (MTBE) and gasoline range hydrocarbons. A liquid stream 26 containing iso-octene and other $C_{5+}$ components is introduced at an upper stage of debutanizer tower 24 to effect separation.

Further upgrading of unreacted components takes place in a second stage reactor containing porous solid acid oligomerization catalyst in a secondary stage catalytic reaction zone, and including means for reacting at least a portion of the first stage effluent unconverted olefins and alcohol fraction under low severity alkylation/oligomerization and etherification conditions at moderate temperature to etherify and/or alkylate/oligomerize methanol, butadiene, and isobutene and form a normally liquid branched hydrocarbon and mono-/dimethyl ethers of butenes while leaving n-alkene recovered from the first stage effluent substantially unreacted. Overhead vapor stream 28, containing unreacted volatile $C_4$- components (isobutene, butadiene, n-butenes, methanol) is heated to moderate reaction temperature in heat exchanger 29 and passed to the secondary reaction zone (II) in reactor 30 for further conversion, as described herein. The $C_{4+}$ olefins may be supplemented optionally with other light olefin feed 27. For instance, propene can co-dimerized with isobutene to produce a normally liquid branched aliphatic hydrocarbon components suitable for gasoline blending are recoverable by absorption/rectification in the second fractionation unit.

Reactor 30 may contain a fluidized bed of solid metal oxide acid catalyst, such as ZSM-5 medium pore aluminosilicate zeolite, which is introduced as fresh or regenerated catalyst via line 31A and removed via line 31B for conventional regeneration or passed for further use in a fluidized catalytic cracking (FCC) unit as auxiliary catalyst. The vapor stream contacts solid catalyst under etherification conditions to obtain MBTE and other $C_5$'s ethers and under moderate oligomerization conditions to convert butadiene, while the n-butene component is less than 20% converted. Under the above reaction conditions, wherein substantially all (ie- greater than 90%) of feedstock butadiene is converted, some etherification and/or alkylation of olefins by methanol and isobutene may occur, depending on catalyst and operating conditions employed.

In a preferred embodiment, an absorber column having distillation/rectification function is operatively connected to receive effluent from the second stage reactor. Advantageously, this includes overhead condenser means for cooling absorber overhead and recovering a n-alkene stream substantially free of iso-alkenes, and means for recycling condensed liquid from the condenser means for contact with second reactor effluent in the absorber column, thereby providing a hydrocarbon liquid rich in branched alkene oligomer in an absorber column bottoms stream. This technique permits operative connection between effluent recovery sections of both stages and provides means for passing the absorber column bottoms stream to the first fractionator column for recovery of normally liquid branched hydrocarbon with ether in the liquid product bottom fractionator stream.

A second intermediate stream 32 containing ethers and $C_{5+}$ hydrocarbons, and other secondary effluent components, such as unreacted $C_4$ hydrocarbons and alcohol is withdrawn from reaction zone 30 and enters the second stage separation unit 36, such as distillation/rectifying column 36. Temperature of second intermediate stream 32 may be reduced prior to entering column 36 or partially condensed therein by contact with cold liquid 37 refluxed by cooling means 38 and employing heat exchanger 40, separator 41 and pump 42. A light n-butene rich stream 39 is recovered substantially free of isobutene, and may be sent for further process (iealkylation) or recycle via line 39A). A liquid stream 26 comprising MTBE and C8 dimer and other $C_{5+}$ oligomers can be withdrawn from column 36 for recovery as product from first column 24 via line 25 along with $C_{5+}$ components of the primary reactor effluent. The liquid stream 26 may be filtered from any fines leaving the fluid bed reactor upstream of the common fractionator, 24.

Regeneration of the solid acid catalyst from reaction zone 30 may be accomplished by procedures well-known in the art. It is feasible to eliminate second stage catalyst regeneration by transporting inactivated fluidized catalyst particles to another process, such as the FCC unit, now shown.

Figure 2:
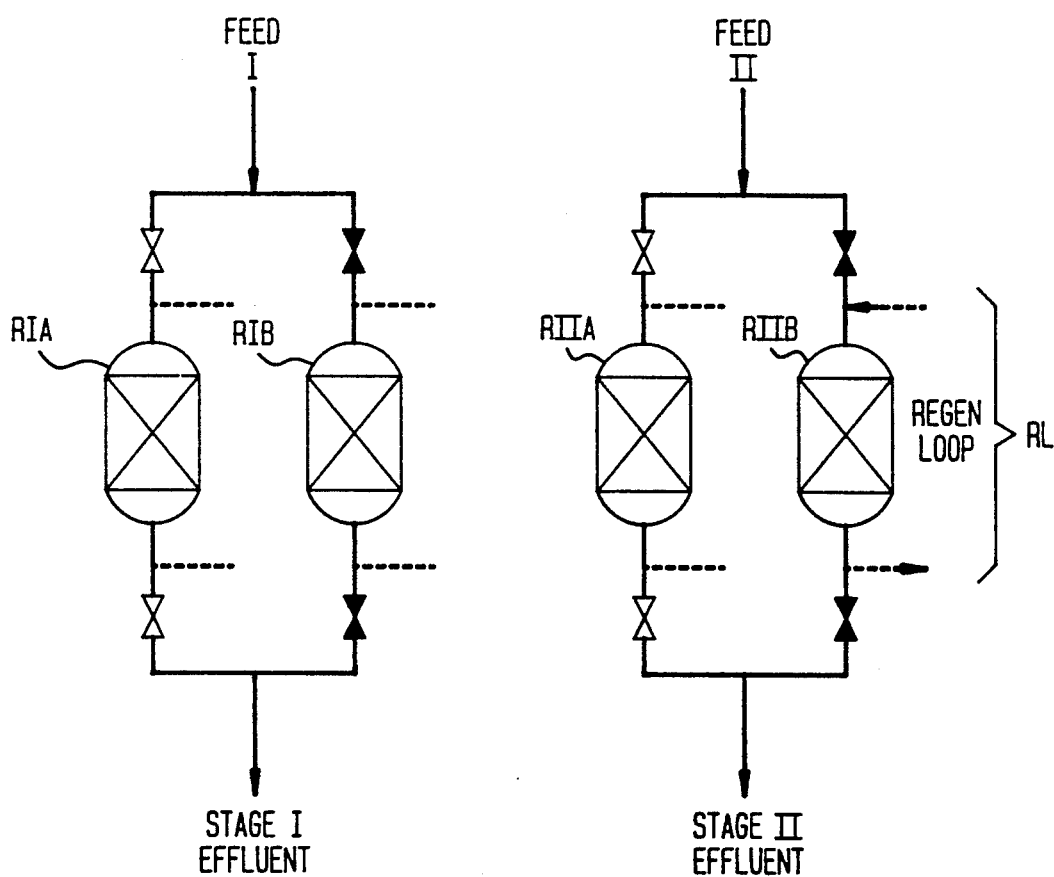

A preferred embodiment is depicted in FIG. 2, employing multiple swing reactors for each stage. The first stage reactor and second stage reactor each comprise a plurality of alternately-connected swing reactor units, RIA, RIB, RIIA, RIIB, containing a fixed bed of regenerable solid catalyst particles. The regeneration loop RL provides means for treating inactivated catalyst employed in the first or second stage by contacting inactivated catalyst with regeneration gas under catalyst regeneration conditions. Conduits and valves provide fluid handling means for operatively connecting one of said swing reactor units from the first or second stage selectively with the regeneration means in a known manner. This reactor structure permits a single regeneration loop to be connected to any of the individual fixed bed process reactors, thus providing an efficient arrangement.

While the invention has been described by specific examples and embodiments, there is no intent to limit the inventive concept except as set forth in the following claims.

I claim:

1. A multistage process for etherifying a mixed $C_4+$ olefinic hydrocarbon feedstock containing diene, isoalkene and n-alkene, comprising:

contacting the olefinic feedstock and aliphatic alcohol in a first reaction stage reaction zone under etherification conditions with acid etherification catalyst to convert a major amount of the isoalkene to $C_5+$ tertiary-alkyl ether;

recovering a reactant effluent from the first stage containing tertiary-alkyl ether product, unreacted alcohol and unreacted olefin comprising n-alkene and diene;

separating an ether-rich $C_5+$ liquid product stream from the first stage effluent in a first product recovery section;

reacting at least a fraction of the first stage effluent unconverted olefins and alcohol fraction under low severity oligomerization conditions comprising moderate temperature between 70° C. and 280° C. and space velocity of 0.5-50 WHSV based on total olefin in the feed in a secondary stage catalytic reaction zone containing porous solid acid oligomerization catalyst particles to oligomerize a major portion of diene;

recovering a $C_5+$ liquid product stream from secondary stage effluent; and recovering n-alkene substantially free of diene from secondary stage effluent.

2. The process of claim 1 wherein the alcohol consists essentially of methanol, the secondary stage catalyst comprises medium pore zeolite and the primary stage catalyst comprises a zeolite or polymeric sulfonic acid resin.

3. The process of claim 1 wherein the mixed olefin feedstock consists predominantly of $C_4$ hydrocarbons containing butadiene, isobutene and n-butene.

4. The process of claim 1 wherein the secondary stage comprises a plurality of fixed bed catalyst zones operatively connected for swing from production mode to regeneration mode in alternating sequence.

5. The process of claim 1 wherein the secondary stage reaction zone comprises a fluidized bed reaction zone for maintaining a solid medium pore zeolite acid particulate catalyst, and further comprising the steps of withdrawing a portion of the solid particulate catalyst from the second stage reaction zone; adding fresh or regenerated catalyst to the second stage reaction zone to maintain acid activity in the bed.

6. The process of claim 1 wherein the aliphatic alcohol is selected from the group consisting of methanol, ethanol, isopropanol or mixtures thereof.

7. The process of claim 1 wherein said secondary stage effluent recovery comprises passing said effluent to a rectifying distillation tower containing a reflux stream comprising said tower overhead comprising condensed n-alkene rich liquid thereby condensing $C_5+$ hydrocarbons.

8. The process of claim 7 wherein said condensed $C_5+$ hydrocarbons from the rectifying tower are passed to said first product recovery section comprising a common distillation tower in conjunction with primary stage effluent, wherein said condensed $C_5+$ hydrocarbons are introduced in an upper portion of said distillation tower and recovered with said first stage product recovery section $C_5+$ liquid product stream.

9. A process according to claim 1 wherein the secondary zone solid acid catalyst particles comprise aluminosilicate zeolite having the structure of ZSM-5, ZSM-11 or zeolite Beta.

10. The process of claim 1 wherein said first product recovery section comprises a distillation column and the distillation column overhead vapor comprises the feed to said secondary stage catalytic reaction zone.

11. The process of claim 5 wherein the second reactor spent catalyst is periodically regenerated with oxygen-containing gas or rejuvenated with a $H_2$ rich stream to maintain the required reactivity.

12. The process of claim 1 wherein said second stage reactor at least a portion of said unreacted alcohol is alkylated or etherified.

13. The process of claim 1 wherein in said second stage reactor at least a portion of iso-alkene in the feed is oligomerized.

14. A multistage process for etherifying a mixed $C_4+$ olefinic hydrocarbon feedstock containing butadiene, isobutene and n-butene, comprising:

contacting the olefinic feedstock and methanol in a first reaction stage reaction zone under etherification conditions with acid etherification catalyst to convert a major amount of the isobutene to $C_5+$ methyl tertiary-butyl ether;

recovering a reactant effluent from the first stage containing ether product, unreacted methanol and unreacted feedstock olefin;

distilling an ether-rich liquid product stream from the first stage effluent in a first product recovery section;

reacting at least a portion of the first stage effluent unconverted olefins and methanol fraction under low severity oligomerization and alkylation conditions comprising moderate temperature between 70° C. and 280° C. and space velocity of 0.5-50 WHSV based on total olefin in the feed in a secondary stage catalytic reaction zone containing porous solid acid oligomerization catalyst particles to react substantially all of the remaining butadiene while reacting less than 20% of n-butene; and recovering a $C_5+$ liquid product stream and a n-butene stream from secondary stage effluent.

15. The process of claim 14 wherein second stage effluent recovery comprises passing secondary stage effluent to a rectifying distillation tower for contact with condensed n-alkene rich liquid reflux, thereby condensing normally liquid hydrocarbons to recover a liquid hydrocarbon stream from secondary stage effluent;

passing condensed liquid hydrocarbon from the rectifying distillation tower to a common distillation tower in the first product recovery section along with primary stage effluent for recovery with the liquid product stream; and recovering n-butene substantially free of butadiene from secondary stage effluent.

16. The process of claim 14 wherein the secondary stage catalyst comprises medium pore zeolite and the primary stage catalyst comprises a zeolite or polymeric sulfonic acid resin, and wherein the mixed olefin feedstock consists essentially of butanes, butadiene, isobutene and n-butene.

17. The process of claim 14 wherein the secondary stage catalytic reactor zone is maintained at low severity oligomerization conditions, comprising reaction temperature of about 50° to 250° C. and space velocity of 0.5–50 WHSV based on total olefins present in the feed.

18. A process according to claim 14 wherein the secondary zone solid acid catalyst particles comprise aluminosilicate zeolite having the structure of ZSM-5, ZSM-11, or zeolite Beta.

19. The process of claim 12 wherein said second stage reactor at least a portion of said unreacted methanol is alkylated or etherified.

20. The process of claim 12 wherein said second stage reactor at least a portion of iso-butene in the feed is alkylated or oligomerized.

* * * * *